(12) United States Patent
Carbune et al.

(10) Patent No.: US 10,397,163 B2
(45) Date of Patent: Aug. 27, 2019

(54) THIRD PARTY APPLICATION CONFIGURATION FOR ISSUING NOTIFICATIONS

(71) Applicant: Google LLC, Mountain View, CA (US)

(72) Inventors: Victor Carbune, Basel (CH); Thomas Deselaers, Zurich (CH); Daniel M. Keysers, Stallikon (CH)

(73) Assignee: Google LLC, Mountain View, CA (US)

( * ) Notice: Subject to any disclaimer, the term of this patent is extended or adjusted under 35 U.S.C. 154(b) by 186 days.

(21) Appl. No.: 15/345,328

(22) Filed: Nov. 7, 2016

(65) Prior Publication Data

US 2018/0131655 A1 May 10, 2018

(51) Int. Cl.
| | | |
|---|---|---|
| *G06F 15/16* | (2006.01) | |
| *H04L 12/58* | (2006.01) | |
| *H04L 29/08* | (2006.01) | |
| *G06Q 50/00* | (2012.01) | |
| *G16H 20/30* | (2018.01) | |

(52) U.S. Cl.
CPC ............ *H04L 51/24* (2013.01); *G06Q 50/01* (2013.01); *H04L 67/20* (2013.01); *G16H 20/30* (2018.01); *H04L 67/22* (2013.01)

(58) Field of Classification Search
CPC ................................ G06Q 50/01; H04L 67/20
USPC ........................................................ 709/206
See application file for complete search history.

(56) References Cited

U.S. PATENT DOCUMENTS

| | | | |
|---|---|---|---|
| 8,938,643 B1 * | 1/2015 | Karmarkar | G06F 11/1658 714/11 |
| 9,043,329 B1 | 5/2015 | Patton et al. | |
| 9,590,942 B1 * | 3/2017 | Yeskel | H04L 51/32 |
| 9,830,400 B2 * | 11/2017 | Taylor | G06F 17/2247 |
| 2004/0034873 A1 | 2/2004 | Zenoni | |
| 2005/0027676 A1 * | 2/2005 | Eichstaedt | G06F 9/542 |
| 2008/0154696 A1 | 6/2008 | Spiegelman et al. | |

(Continued)

FOREIGN PATENT DOCUMENTS

WO WO 2008/015187 2/2008

OTHER PUBLICATIONS

International Search Report and Written Opinion issued in International Application No. PCT/US2017/051554, dated Dec. 5, 2017, 8 pages.

(Continued)

*Primary Examiner* — Anthony Mejia
(74) *Attorney, Agent, or Firm* — Fish & Richardson P.C.

(57) ABSTRACT

Methods, systems, and apparatus, including computer programs encoded on a computer-readable storage medium for implementing one or more application programming interfaces (APIs) that configure applications stored in an electronic device are described. An application may be configured to receive event information from various sources based on user preferences and application permissions. In response to receiving the event information, the app may determine whether a notification should be issued to a user. This determination may be made based on various factors such as the type of event, user history, contextual data, ranking data, and application permissions. The notifications may include one or more of messages to the user and recommended actions for consideration by the user. The actions may include sharing data with other users who share a presence or interest in an event with the user.

20 Claims, 5 Drawing Sheets

(56) References Cited

U.S. PATENT DOCUMENTS

| | | | |
|---|---|---|---|
| 2009/0319472 A1 | 12/2009 | Jain et al. | |
| 2010/0049737 A1 | 2/2010 | Ambrosio | |
| 2010/0274691 A1 | 10/2010 | Hammad | |
| 2011/0060996 A1* | 3/2011 | Alberth, Jr. | H04L 51/24 |
| | | | 715/736 |
| 2012/0143845 A1* | 6/2012 | Jiang | G06F 16/951 |
| | | | 707/710 |
| 2012/0271676 A1 | 10/2012 | Aravamudan et al. | |
| 2012/0295645 A1* | 11/2012 | Yariv | H04L 67/322 |
| | | | 455/466 |
| 2013/0031190 A1* | 1/2013 | Chan | G06Q 30/02 |
| | | | 709/206 |
| 2013/0132896 A1 | 5/2013 | Lee et al. | |
| 2013/0173728 A1 | 7/2013 | Starenky et al. | |
| 2013/0212176 A1 | 8/2013 | Koulomzin et al. | |
| 2013/0316744 A1 | 11/2013 | Newham | |
| 2014/0359026 A1* | 12/2014 | Lefor | H04L 51/14 |
| | | | 709/206 |
| 2017/0177807 A1* | 6/2017 | Fabian | G06Q 10/087 |
| 2017/0214643 A1* | 7/2017 | Shukla | H04L 51/10 |

OTHER PUBLICATIONS

Office Action and Search Report issued in British Application No. GB1715080.6, dated Feb. 28, 2018, 12 pages.

Conger, "Facebook says it's not making friend suggestions based on your location after all," TechCrunch, Jun. 28, 2016 [retrieved on Oct. 6, 2016]. Retrieved from the Internet: URL<https://techcrunch.com/2016/06/28/facebook-says-its-not-making-friend-suggestions-based-on-your-location-after-all/>, 7 pages.

Cook et al., "Detection of Social Interaction in Smart Spaces," Cybern Syst., 41(2):90-104, Feb. 1, 2010.

Do et al., "Human Interaction Discovery in Smartphone Proximity Networks," Personal and Ubiquitous Computing 17(3):413-431, Mar. 2013.

Dong et al., "Multiscale event detection in social media," Data Min Knowl Disc, 29:1374-1405, Jun. 2015.

Li et al., "Multi-Modal In-Person Interaction Monitoring Using Smartphone and On-Body Sensors," 2013 IEEE International Conference on Body Sensor Networks, pp. 1-6, May 2013.

GB Office Action issued in British Application No. GB1715080.6, dated Dec. 4, 2018, 4 pages.

\* cited by examiner

THIRD PARTY APPLICATION CONFIGURATION FOR ISSUING NOTIFICATIONS

FIELD

This disclosure generally relates to configuration of third-party applications in electronic devices.

BACKGROUND

Users participating in an event often wish to share messages and notifications about the event with other friends using third-party applications (apps). For example, users may wish to text each other or share pictures when the users are present at the same event. However, users currently experience several inconveniences in sharing messages and notifications using third-party apps.

SUMMARY

According to some implementations, third-party apps executed in an electronic device may be configured using one or more application programming interfaces (APIs). A third-party app may be configured to receive event information from one or more sources based on user preferences and permissions of the app. In response to receiving the event information, a determination is made as to whether a notification should be issued to a user. This determination is made based on various factors such as the type of event, a notification trigger for the event, user history, contextual data, ranking data, and app permissions. The notifications may include one or more of messages to the user and recommended actions to be considered by the user. The actions may include sharing data with other users who share a presence or interest in an event with the user.

According to some implementations, a smart notification generator may be trained using neural networks or other machine-learning techniques to determine whether or not a notification should be issued to the user. The smart notification generator may be trained using various suitable data such as, for example, data corresponding to user preferences and settings, user history of responding to event information and notifications, social network trends, and app updates.

Innovative aspects of the subject matter described in this specification include, in some implementations, a computer-implemented method to perform operations. The operations include transmitting, by one or more processors, a request to confirm registration of an application with one or more data sources. In response to receiving an indication that the application is registered with the one or more data sources, event information is received from the one or more data sources, and a determination is made that a trigger event associated with the application has occurred. The operations further include determining, by the one or more processors, whether to output a notification including data corresponding to the event information based on one or more criteria, and in response to determining that the one or more criteria is satisfied, determining to output the notification including data corresponding to the event information. The operations further include providing, by the one or more processors, the notification including the data corresponding to the event information to a display of a user device.

Implementations may each optionally include one or more of the following features. For instance, in some implementations, the operations further include training, by the one or more processors, a notification generator to determine whether or not to output the notification using training data. The training data includes one or more of rules and permissions associated with the application, user preference data, user history data, and application trends.

In some implementations, the operations further include determining, by the one or more processors, user preferences associated with the application, and determining, by the one or more processors, information that is likely to be of interest to the user based on the user preferences associated with the application, in response to receiving an indication that the application is not registered with the one or more data sources. The operations also include transmitting a request to register the application with the one or more data sources. The request to register the application with the one or more data sources includes a request for data corresponding to the information that is likely to be of interest to the user.

In some implementations, the operations further include determining, by the one or more processors, applications stored on the user device, and determining, by the one or more processors, application permissions and a trust level associated with each of the applications stored on the user device. In response to receiving an indication that the application is not registered with the one or more data sources, the operations further include determining, by the one or more processors, that receiving information from the one or more data sources satisfies the application permissions and the trust level for the application, and transmitting a request to register the application with one or more data sources.

In some implementations, the trigger event associated with the application includes one or more of: a user action, expiration of a time period associated with the application, satisfaction of a condition set by rules of the application, and addition of data in the one or more data sources.

In some implementations, the operations further include receiving an indication of a user selection at the user device in response to providing the notification to the display of the user device, and training, by the one or more processors, a notification generator to determine whether or not to output the notification using the user selection.

In some implementations, the operation of providing, by the one or more processors, the notification including the data corresponding to the event information includes selecting a template from a plurality of templates based on a type of the application, and providing template data corresponding to the selected template to generate the notification.

Other implementations of these aspects include corresponding systems, apparatus, computer-readable storage mediums, and computer programs configured to implement the actions of the above-noted methods.

Implementations described in this specification provide one or more of the following advantages. In some implementations, a user may be relieved of the inconvenience of configuring third-party apps to execute certain operations or to manually make selections and inputs to command a user device to share messages, execute operations, or issue notifications. Instead, by utilizing machine learning techniques, user devices may automatically configure third-party apps to timely generate relevant notifications based on user behavior and preferences, and share data with the user's friends and contacts that are in the vicinity of the user.

For example, in some implementations, a user does not have to search for references and sources where the user may be able to find information of interest to the user. Rather, a third-party application is automatically configured to receive information that is of interest to the user from a data source.

In some implementations, a user does not have to make selections or inputs to command an app in the user device to take an action. Rather, the app may automatically issue a notification to ask the user if the user would like the app to take an action. The app is configured, in part, based on user circumstances, user location, user historical preferences and behavior, and app rules. In some cases, the user device will not ask the user for permission, and may automatically take one or more actions. This process is more convenient for the user and allows actions to be executed more quickly and efficiently without necessarily relying on explicit selections or inputs from the user to initiate an action.

In some implementations, by detecting a user's friends and contacts who are in the vicinity of the user or who share an event with the user, a user device may automatically configure notifications and actions to enable the user to interact more efficiently with the user's friends and contacts who are in the vicinity of the user or who share an event with the user.

The details of one or more implementations are set forth in the accompanying drawings and the description below. Other features and advantages will become apparent from the description, the drawings, and the claims.

BRIEF DESCRIPTION OF THE DRAWINGS

Like reference numbers and designation in the various drawings indicate like elements.

DETAILED DESCRIPTION

Figure 1:
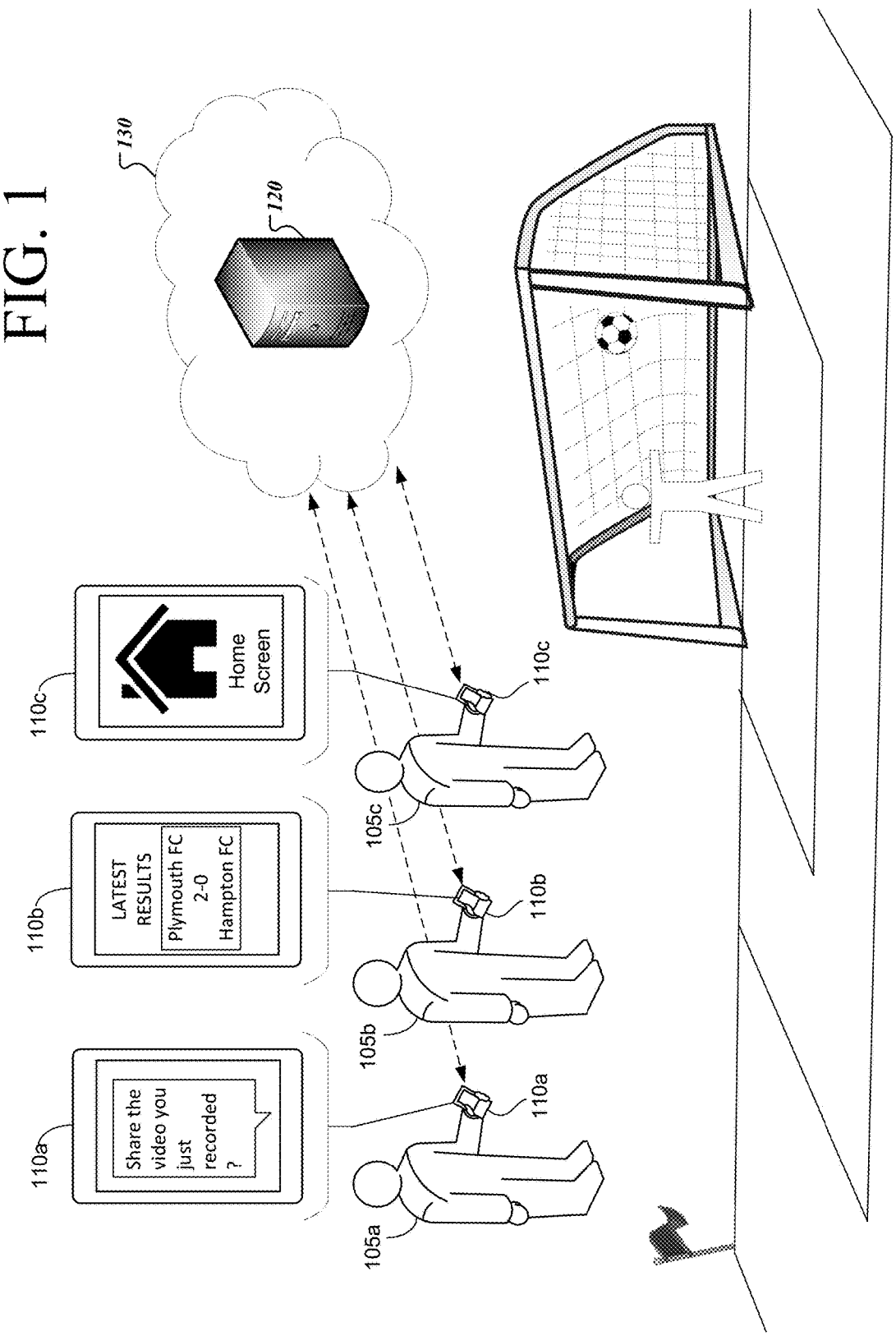
FIG. 1 depicts an exemplary scenario in which third party apps are configured in multiple user devices to execute different operations in the same location.

In the exemplary scenario illustrated in FIG. 1, multiple users 105a, 105b, 105c are attending a sporting event, such as a soccer game. Each user 105a, 105b, 105c is in possession of a respective user device 110a, 110b, 110c. The user devices 110a, 110b, 110c may communicate with a network 130 that includes one or more servers 120. Of the three users, user 105b is interested in receiving live score updates, and user 105a frequently shares videos on the user's social media platform. User 105c is not interested in sports, but is attending the sporting event as a friend of users 105a and 105b.

Each of the user devices 110a, 110b, 110c may include one or more APIs for configuring third party apps. The apps may be configured based on various factors including user choices and preferences. For example, because user 105b is interested in sports, an API may configure a third party sports app on user device 110b to request a sports database or news source to provide sports updates and news to the user device 110b. In another example, if a user, such as user 105c, frequently checks the weather, an API may configure a third party weather app on user device 110c to request a weather database or source to provide weather updates and news to the user device 110c.

In general, a third-party app may be any app that is not installed in an electronic device by a developer of an operating system in the electronic device. A third-party app may be installed or stored on an electronic device using various suitable methods. For example, in some cases, a user may install an app using data obtained from a network such as the Internet. In some cases, an electronic device may install an app using data obtained from a storage disk.

When a third-party app is written by a developer, the app may not be customized for individual users. For example, the app may obtain general information for basic functions of the app and for generic users of the app, but, in many cases, may not be able to provide information that is customized according to the preferences and tastes of individual users. In addition, the reliability of some apps may be uncertain and users may not want unverified or untrusted apps to access more than a minimal amount of user information. Implementations described in this specification with reference to the figures address these and other problems associated with third-party apps.

To receive information, such as updates and news, an app configured by an API may register a user device with a server or database associated with the source of information. For example, in FIG. 1, an app in user device 110b may send a request to one or more servers 120 associated with a sports information database to register user device 110b. As a result of the registration, user device 110b may receive sports updates through the third-party sports app. Details of the registration process are provided in further detail below.

In some implementations, different levels of information may be requested. For example, in some cases, an app in user device 110b may request general sports information. In some cases, an app in user device 110b may request information pertaining to a particular sport, such as soccer. In some cases, an app in user device 110b may request information pertaining to a particular team.

Apps in the user devices 110a, 110b, 110c may also control notifications that are presented to the users 105a, 105b, 105c upon detection of a trigger event. A trigger event may be one or various types of occurrences, conditions, or events. For example, in some cases, a trigger event may include detection of a particular environment, for example, a sports stadium, a college campus, a house, a beach, or a museum. In general, an environment may include a virtual environment, a physical environment, or a mixed environment which includes both virtual and physical environments. A physical environment may refer to any physical venue or location suitable for hosting an event. A virtual environment may refer to various suitable digital interfaces such as virtual meetings, online gaming sessions, audio and/or video teleconferencing, or digital broadcasts sessions. An example of a mixed environment includes a scenario in which two conference rooms are connected via a virtual meeting with several people in each conference room.

In some cases, a trigger event may include detection of multiple users within a threshold distance of a user device. In some cases, a trigger event may include detection of weather conditions, e.g., rain or snow, or time of day, e.g., morning, evening, or night. Trigger events may be programmed by an app developer, a user of a user device, or may be programmed based on machine learning. Multiple factors such as, for example, user history, user input, user preferences, contextual information, timing of the trigger event, and type of event may be used to set trigger events.

Referring to FIG. 1, user 105a uses device 110a to record action on the field that resulted in a goal. User 105a terminates the recording after the goal is scored. After the goal is scored, a notification is displayed on user device 110a asking the user 105a if the user 105a would like to share the video with friends in the user's social media platforms. This notification is output because the user device 110a detected a trigger event corresponding to a shared event in which user 105a is at a stadium with other friends in his social network and because the user has a history of sharing videos after recording them. In general, a shared event may be any event in which at least two users are associated with the same event. An API in user device 110a may enable the user device 110a to display a notification asking user 105a if user 105a would like to share the video with friends in the user's social network or users 105b and 105c who are in the user 105a's vicinity.

User device 110b may also receive a notification after the goal is scored. In particular, user device 110b receives an update on the latest results of a soccer match. The user device 110b receives this notification because one or more apps in user device 110b have registered the user device 110b to receive live updates for soccer matches, and have determined that the latest update of the game between Plymouth FC and Hampton FC is a game that the user is currently attending and interested in. In some implementations, user device 110b may receive the update information, but does not display a notification including the update information because the user device 110b determines that user 105b is likely located at the stadium where the match is being played and the update information is likely to provide information user 105b is already aware of.

In the scenario illustrated in FIG. 1, user device 110c does not display any notification and maintains a display of a home screen because no trigger event has been detected or user device 110c. As shown in the exemplary scenario of FIG. 1, third-party apps may be configured differently by one or more APIs on different devices based on user interests and preferences, and may provide notifications based on the respective configurations.

Figure 2:
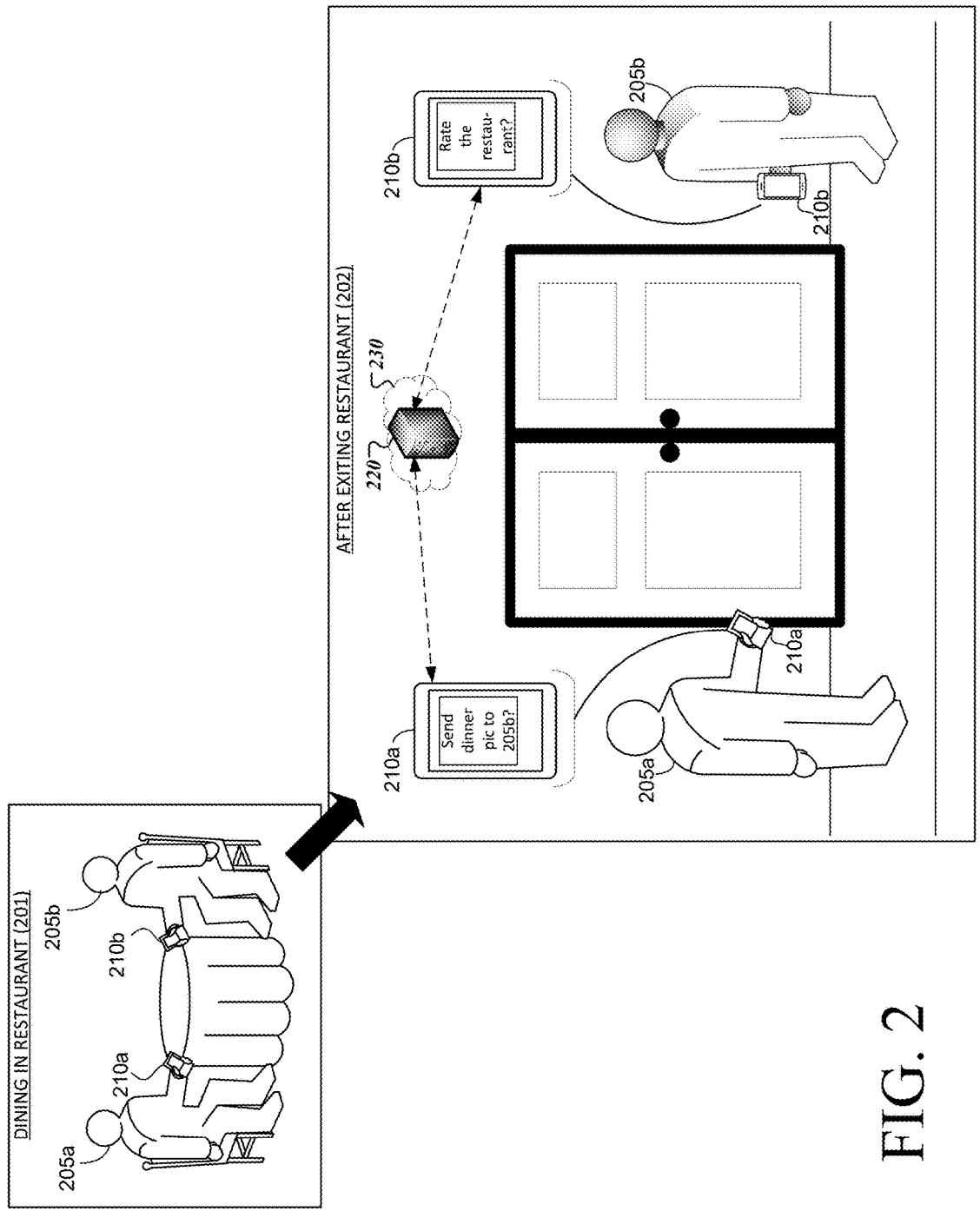
FIG. 2 depicts an exemplary scenario in which third party apps are configured in multiple user devices to execute different operations upon the satisfaction of a trigger event.

Referring to the exemplary scenario depicted in FIG. 2, users 205a and 205b are dining in a restaurant (201). User devices 210a and user devices 210b may detect the presence of users 205a and 205b through various suitable methods including extracting data from social networks to determine the location of other users, using location based services to identify the location of devices 210a and 210b, or using short distance communication between the devices 210a and 210b to exchange location information. After dinner, users 205a and 205b exit the restaurant (202). The restaurant exit is a trigger event that triggers user devices 210a and 210b to display notifications.

In particular, while dining (201), user device 210a may determine that user 205a is dining at the restaurant using any suitable location determining service or a user input specifying one or more of the user's activity and location. User 205a may take pictures during the dinner. The user device 210a may subsequently determine that the user 205a has exited the restaurant using any suitable location determining service, data from motion sensors indicative of the user's movement, or a user input specifying the user's restaurant exit or location (202).

User device 210a includes one or more APIs that have configured a third-party photo sharing app to share, upon satisfaction of a trigger event, pictures with a dining-related tag, or pictures with metadata indicating an image capture time that is within a predetermined time period of user 205a's exit from the restaurant. The picture may be shared with users who are identified as participating in the event with the user.

In scenario 201 illustrated in FIG. 2, the user device 210a determines that user 205b was present at the dinner with user 205a; determines that user 205a exit the restaurant; determines that the restaurant exit corresponds to a trigger event for a third-party photo sharing app; and generates a notification corresponding to the trigger event and third-party photo sharing app. As shown, user device 210a displays a notification asking user 205a whether the user 205a would like to send dinner pictures to the user, i.e., user 205b, who user 205a had dinner with.

As noted above, user device 210b also displays a notification to user 205b. In particular, while dining (201), user device 210b may determine that user 205b is dining at the restaurant using any suitable location determining service or a user input specifying one or more of the user's activity and location. The user device 210b may subsequently determine that the user 205b has exited the restaurant using any suitable location determining service, data from motion sensors indicative of the user's movement, or a user input specifying the user's restaurant exit or location (202).

User device 210b includes one or more APIs that have configured a third-party restaurant rating app to request the user for a restaurant rating upon satisfaction of a trigger event, which in this scenario corresponds to user 205b's exit of a restaurant. The one or more APIs may have configured the third-party restaurant rating app based on user 205b's frequent habit of rating restaurants shortly after dining at restaurants.

In scenario 201 illustrated in FIG. 2, the user device 210b determines that user 205a was present at the dinner with user 205b; determines that user 205b exit the restaurant; determines that the restaurant exit corresponds to a trigger event for a third-party rating app; and generates a notification corresponding to the trigger event and third-party restaurant rating app. As shown, user device 210b displays a notification asking user 205b whether the user 205b would like to rate the restaurant. In some cases, after completing the rating, user device 210b may also display a notification inquiring whether user 205b would like to share the rating with user 205a.

Although the above-noted implementations in FIGS. 1 and 2 have been described with user devices making various determinations such as the determination of whether a trigger event is satisfied and whether a notification should be displayed in response to the satisfaction of a trigger event, in some implementations, these determination steps may be performed by a network server. In such implementations, the network server may receive data from the user devices, may make the determinations, and provide data to the user devices to display notifications. For example, in FIG. 1, server 120 in network 130 may make the determinations. In FIG. 2, server 220 in network 230 may make the determinations.

Figure 3:
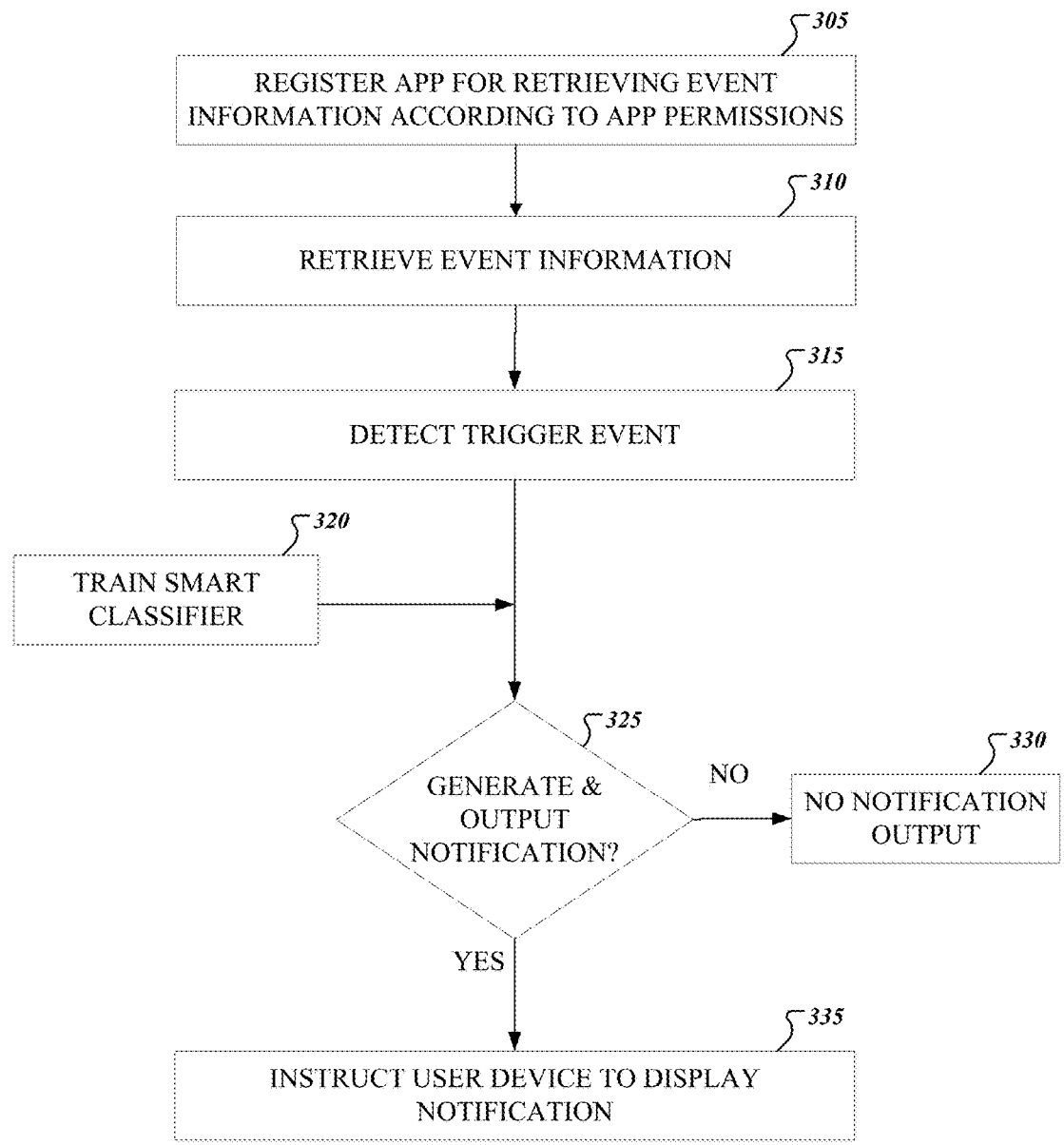
FIG. 3 depicts a flowchart illustrating a method for configuring a third party app using one or more APIs.
Figure 5:
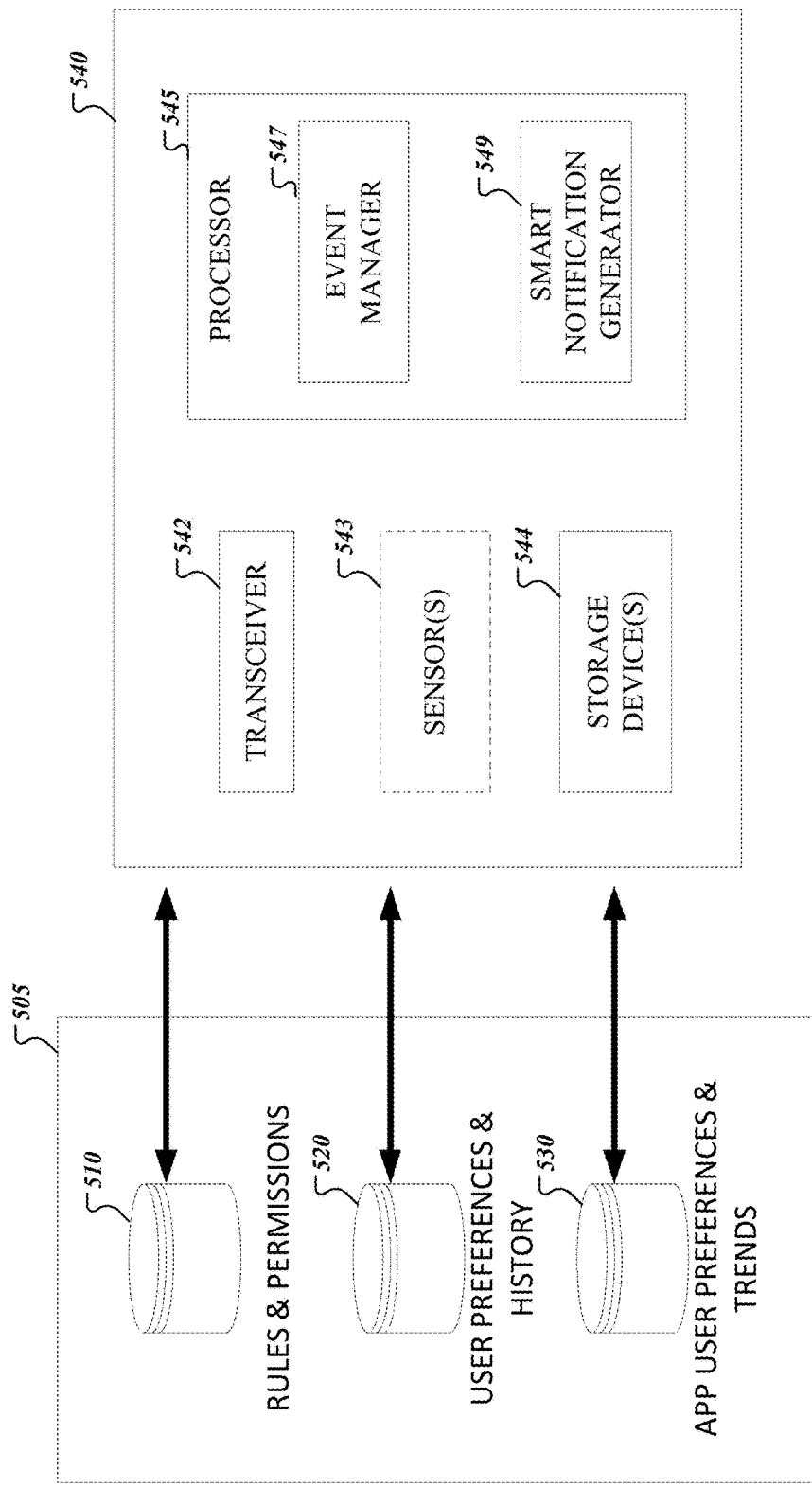
FIG. 5 depicts a system for configuring a third party app using one or more APIs.

FIG. 3 illustrates a method for configuring third party apps using one or more APIs. This method may be used to implement the scenarios described above with respect to FIGS. 1 and 2. The method of FIG. 3 may be implemented by the system illustrated in FIG. 5. The system includes an electronic device 540 and network databases 505. The electronic device 540 includes a transceiver 542, one or more storage devices 544, and a processor 545 that includes an event manager 547 and a smart notification generator 549. In some implementations, each of the event manager 547 and the smart notification generator 549 may be implemented, at least in part, by an API. The network databases 505 include a rules and permissions database 510, a user preferences and history database 520, and an app user preferences and trends database 530. In some implementations, electronic device 540 also includes one or more sensors 543.

The event manager 547 may determine the number and types of apps installed in a user device, and a trust level associated with each app. Trust levels of an app may be determined by various factors including, for example, a classification of the app by an app store, feedback and reviews by users, metadata attached to the app, and the existence of malicious code in the app. For example, if an app is downloaded from a trust worthy app store such as Google's Play Store, user feedback and reviews are generally positive, and no reports of malicious code being embedded in the app code have been located, then the app may be classified as a trust worthy app and assigned a high trust level. If an app has some complaints by users of crashes or malicious code being embedded in the app code, then the app may be assigned a low trust level.

In general, various levels of trust may be used. Each level of trust is mapped to a set of permissions. Apps having a high trust level may be granted more permissions and permissions that allow greater access to user information and components of the electronic device 540. Apps having a low trust level may be granted less or minimal permissions and permissions that limit access to user information and components of the electronic device 540.

In some implementations, the trust level associated with an app may change over time. For example, if an app is initially assigned a low trust level, is executed multiple times, but no problems are reported as a result of the executions, the trust level assigned to the app may be raised to a higher level. In another example, if an app is initially assigned a high trust level, is executed multiple times, but several problems are reported as a result of the executions, the trust level assigned to the app may be dropped to a lower level. Permissions granted to an app may be changed in accordance with the changing trust levels.

After a third-party app and its trust level is determined, the event manager 547 may register the app according to permissions associated with the app and according to user preferences (305). The event manager 547 may access the rules and permissions associated with the app from the rules and permissions database 510. The rules and permissions database 510 stores a mapping of permissions granted to apps and permissions corresponding to trust levels of apps. Upon receiving information identifying an app and a trust level associated with the app from the electronic device 540, the rules and permissions database 510 may access the mapping and provide permission information for the identified app to the electronic device 540. As noted above, the rules and permissions correspond to the determined trust level such that apps with higher trust may have a greater number of permissions to access user information and the electronic device 540.

The event manager 547 may also access user preferences and history of actions from the user preferences and history database 520. The user preferences and history database 520 may store data indicative of user behavior and choices without storing information that identifies the user. In some implementations, the user preferences and history database 520 may store various data including, for example, data indicative of locations of a user device associated with the user, data indicative of user selections and interactions with apps and the Internet, data indicative of the user's social network, social actions or activities, and data indicative of the frequency of use of apps and frequency of functions executed by the used apps.

In general, users may be provided with an opportunity to control whether, when, and how the user preferences and history database 520 collects user information. In addition, some or all of the data associated with a user may be anonymized in one or more ways before it is stored or used, so that personally identifiable information is removed. For example, a user's identity may be anonymized so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and how user information is used by the user preferences and history database 520.

After retrieving user preferences and history of actions from the user preferences and history database 520, the event manager 547 may determine or identify interests of the user. For example, the event manager 547 may determine or identify social events, friends, or sports that a user may be interested. In some implementations, the event manager 547 may determine or identify actions that the user frequently takes in certain circumstances. For instance, referring to FIG. 2, the event manager 547 may determine that a user frequently likes to rate restaurants after visiting the restaurants, or, referring to FIG. 1, that a user is interested in a particular sport, such as soccer.

As noted above, based on the user's preferences and permissions associated with an app, the event manager 547 may register the app with one or more data sources to receive information from the data sources (305). For example, the event manager 547 may register an app with a sports database to receive information about sports the user may be interested in. In the example shown in FIG. 1, the event manager 547 registered a sports app with a data source that provided updates on soccer results. In another example, if a user is determined to be interested in recipes, the event manager 547 may register a third-party food app on the user device to receive new recipes as recipes are added to a recipe database. In general, a data source may refer to various types of sources that can provide information such as, for example, a database, a web site, a storage unit, a server, or a computer.

In some implementations, as part of operation 305, when determining the number and types of apps installed in a user device and a trust level associated with each app, the event manager 547 may confirm whether each determined app is already registered with one or more data sources by sending a confirmation request message to the data sources. The confirmation request message may request a verification or acknowledgement of app registration from the data sources. If no verification or acknowledgement is received within a threshold period of time of transmitting the confirmation request message, the event manager 547 may determine that the app is not registered with the data sources to which the confirmation request message was transmitted. If an app is not registered with one or more data sources, the event manager 547 may register the app with the data sources based on the user's preferences and permissions as described above. If the app is already registered with one or more data sources, the event manager 547 may execute operation 310 as described below.

The registration process may include transmitting a registration request message for registering a user device to the one or more data sources, and receiving an acknowledgement from the one or more data sources that the user device and application in the user device have been registered. The transmitted registration request message may include user device identification and address information so that the one or more data sources can transmit information to the user device over a network. The transmitted registration request message may also include information identifying an app for which the registration request is being sent. In some implementations, the transmitted registration request message may also include setting information that includes timing information indicating how often the user device would like to receive information, content information indicating a type of content to be transmitted to the user device, or format information indicating a format in which the information may be transmitted or provided to user device.

After registering the app with one or more data sources or confirming that the app is registered with one or more data sources, the electronic device 540 may receive information from the one or more data sources (310) and the event manager 547 may detect whether a trigger event occurred (315). A trigger event may vary according to the type of app. In some cases, a trigger event associated with a particular app may be based on a user action such as receiving a user input or request for displaying information. In some cases, a trigger event may be based on data received from the data source. For instance, a trigger event associated with a particular app may correspond to new information such as a new recipe or updated scores received from data sources.

In some cases, a trigger event associated with a particular app may be determined by the rules of the app. For instance, an app may be programmed to generate a notification or provide information to a user periodically or after a predetermined time period. The trigger event in these cases is detected when the predetermined time period expires. In some cases, a trigger event associated with a particular app may be based on user location or circumstances. For example, a trigger event for an app may occur when a user is located within a threshold distance of one or more people or a particular location. The threshold distance may be set by an app developer or the user; may be configured by machine learning, or may be specified by app rules and permissions. In general, an app may have any number of trigger events.

In response to detecting a trigger event, the smart notification generator 549 determines whether to generate and output a notification (325). The smart notification generator 549 may make this determination based, at least in part, on its training. The smart notification generator 549 may be trained continuously or periodically with training data (320). In some implementations, various machine learning algorithms, neural networks, or rules may be utilized along with training data to train and operate the smart notification generator 549.

Training data may be obtained from any of the network databases 505. The user preferences and history database 520 may provide user preferences and history of actions, as noted above. The user preference and history of actions data may be used as training data that the smart notification generator 549 may use to determine whether to generate and output a notification. For example, if user preference and history of actions data indicates that a user has ignored a threshold number of previous updates, such as weather updates, the smart notification generator 549 may determine that the user is not interested in viewing weather updates, and may decide against generating a weather update notification when new weather-related information is received.

The app user preferences and trends database 530 may provide data that indicates trends and preferences of a plurality of users of the app. For example, an app server may monitor which functions of the app are frequently executed by app users, information that is frequently requested, or information that is frequency rejected by cumulative users of the app. This information may be stored in the app user preferences and trends database 530 and may be used as training data to train the smart notification generator 549. For example, if app user preferences and trends data indicates that most users of an app, such as a traffic app, have viewed traffic update notifications but ignored notifications including accident reports, the smart notification generator 549 may determine not to generate notifications including accident reports, but may generate and output traffic update notifications.

The rules and permissions database 510 may provide data that indicates various rules and permissions associated with outputting notifications. For example, the rules and permissions database 510 may provide data indicative of the timings of notifications, the number of notifications, and the types of notifications that an app may output. The rules and permissions database 510 may also prevent information that is not related to an app from being output in a notification. The app rules and permissions data may be used as training data to train the smart notification generator 549. For example, if app rules and permissions data for an app indicate that only two notifications can be output in a certain time period, for instance six hours, then the smart notification generator 549 may not permit any more than two notifications to be output in a six hour period.

In some implementations, the smart notification generator 549 may include a ranking engine which may rank generated notifications and select a determined number of highest ranked notifications for output. For example, received event information and the detected trigger event may result in multiple notifications being generated. Training data may, for instance, indicate that rules of the app only permit one notification to be output at a time, or indicate that a user may have a history of only viewing one notification at a time. Accordingly, based on the training data, the smart notification generator 549 may activate the ranking engine to rank the generated notifications. Notifications may be ranked based on the likelihood of a user viewing the notification. The likelihood of a user viewing a notification is based on the training data. The smart notification generator 549 may then select a determined number of highest ranked notifications for output. The number of highest ranked notifications that can be output may be set by app rules or permissions, by an app developer, or by the user.

Based on the training data and in response to detecting a trigger event, the smart notification generator 549 determines whether to generate and output a notification (325). If the smart notification generator 549 determines not to generate or output a notification, no output is generated and a user does not receive any notification (330). If the smart notification generator 549 decides to generate and output a notification, the processor 545 may generate instructions and data for the user device to display a notification corresponding to the received event information (335).

Figure 4:
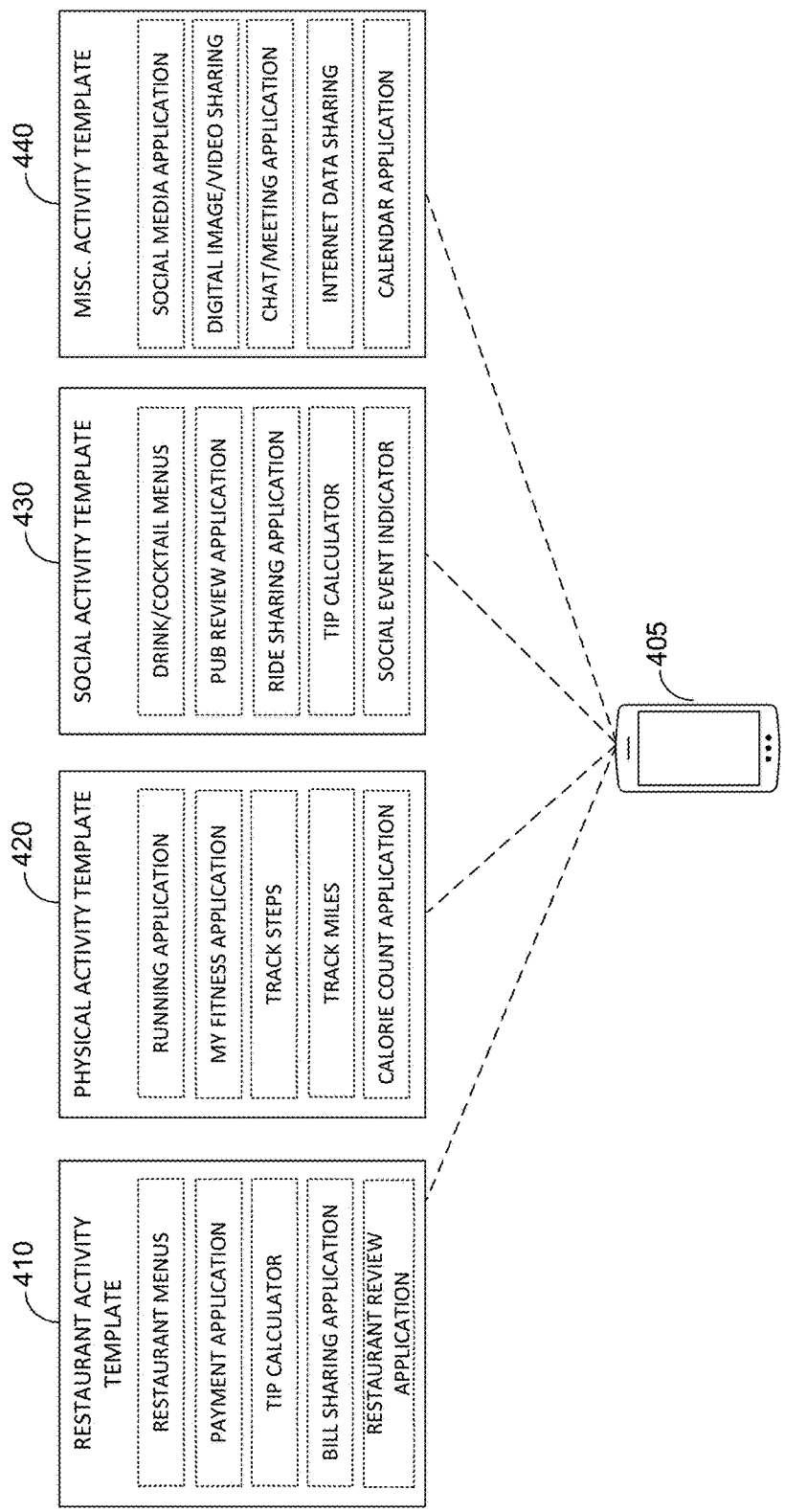
FIG. 4 depicts templates used for generating notifications.

The user device may display a notification using one or more output templates. FIG. 4 illustrates exemplary notification templates 410, 420, 430, 440 that may be selected by the electronic device 540 to generate a notification based on the type of app for which a trigger event is detected. Output activity templates 410, 420, 430, 440 can each include multiple templates corresponding to multiple notification types and apps. For example, the restaurant activity template 410 may be used for notifications related to outputting restaurant menu content and tip calculation content, or notifications to be provided by a payment app, a bill sharing app, or a restaurant review app. Although FIG. 4 only shows a physical activity template 420, a social activity template 430, and a miscellaneous activity template, various suitable notification templates may be used in any suitable manner.

After a notification is displayed on the user device, a user may ignore the notification, view the notification, or take some additional action in response to the notification. For example, referring back to FIG. 1, if the notification is a score update for a third-party sports app, the user 105b may view the score update and take no further action. User 105a may receive a notification in the form of a question asking the user 105a whether the user 105a would like to take additional action to share a video. If the user 105a responds affirmatively indicating that the user 105a would like to take additional action, in some cases, the user device 110a may prompt the user 105a to select one or more contacts with whom the user 105a would like to share the video.

In some implementations, data indicating the user response to the notification is provided to the user preferences and history database 520 and used as training data for the smart notification generator 549. As noted above, this information may be handled in a manner that anonymizes data and does not include user identification information.

Referring back to FIG. 5, in some implementations, all the components of the system may be implemented in a user device. In some implementations, all the components of the system may be implemented in a network server. In some implementations, the components of the system may be distributed across a network such that some components are implemented in a network server and some components are implemented in a user device. For example, transceiver 542, one or more sensors 543, one or more storage devices 544, and a processor 545 may be implemented in a user device, and the rules and permissions database 510, user preferences and history database 520, and app user preferences and trends database 530 may be implemented in a network server. In implementations in which the electronic device 540 is implemented in a user device, the electronic device 540 may refer to any suitable electronic device that has a processor and can connect to a network. Examples of the electronic device 540 include, but are not limited to, a desktop, lap top, personal digital assistant, electronic pad, electronic notebook, telephone, smart phone, television, smart television, watch, smart refrigerator. In implementations in which the electronic device 540 is implemented in a network server, examples of the electronic device 540 include, but are not limited to, a work station, server, blade server, or mainframe.

The transceiver 542 in the electronic device 540 may include a transmitter and a receiver and may be utilized to communicate with one or more network servers, and one or more databases. The transceiver 542 may include amplifiers, modulators, demodulators, antennas, and various other components. The transceiver 542 may direct data received from other network components to other components in the electronic device 540 such as the processor 545. The transceiver 542 may also direct from components in the electronic device 540 to other devices in in the system.

In some implementations, the electronic device 540 may also include one or more sensors 543, which may include various suitable sensors such as touch sensors, capacitive sensors, optical sensors, and motion sensors. Data received from the sensors 543 may be used to provide various types of information. For example, touch, optical, or capacitive sensors may be used to determine whether a user is touching a display to make a selection. The motion sensors may be used to determine a direction, displacement, or velocity of the electronic device 540's movement. The optical sensors may be used to determine the lighting conditions around the electronic device 540.

The one or more storage devices 544 may include one or more mass storage devices such as, for example, magnetic, magneto optical disks, optical disks, EPROM, EEPROM, flash memory devices, and may be implemented as internal hard disks, removable disks, magneto optical disks, Programmable Logic Devices (PLDs), CD ROM, or DVD-ROM disks for storing data. In some implementations, the one or more storage devices 544 may store one or more of rules for detecting trigger events, rules for selecting output templates, and training data for training the smart notification generator 549.

In some implementations, the electronic device 540 and network databases 505 may be connected through one or more networks. The one or more networks may provide network access, data transport, and other services to the system, one or more network servers, and one or more databases. In general, the one or more networks may include and implement any commonly defined network architectures including those defined by standards bodies, such as the Global System for Mobile communication (GSM) Association, the Internet Engineering Task Force (IETF), and the Worldwide Interoperability for Microwave Access (WiMAX) forum. For example, the one or more networks may implement one or more of a GSM architecture, a General Packet Radio Service (GPRS) architecture, a Universal Mobile Telecommunications System (UMTS) architecture, and an evolution of UMTS referred to as Long Term Evolution (LTE). The one or more networks may implement a WiMAX architecture defined by the WiMAX forum or a Wireless Fidelity (WiFi) architecture. The one or more networks may include, for instance, a local area network (LAN), a wide area network (WAN), the Internet, a virtual LAN (VLAN), an enterprise LAN, a layer 3 virtual private network (VPN), an enterprise IP network, corporate network, or any combination thereof.

In some implementations, the one or more networks may include a cloud system, one or more storage systems, one or more servers, one or more databases, access points, and modules. The one or more networks including the cloud system may provide Internet connectivity and other network-related functions.

The one or more servers may communicate with system to implement one or more operations of the third-party app configuration method described herein. The one or more servers may include any suitable computing device coupled to the one or more networks, including but not limited to a personal computer, a server computer, a series of server computers, a mini computer, and a mainframe computer, or combinations thereof. For example, the one or more servers may include a web server (or a series of servers) running a network operating system.

The one or more servers may also implement common and standard protocols and libraries, such as the Secure Sockets Layer (SSL) protected file transfer protocol, the Secure Shell File Transfer Protocol (SFTP)-based key management, and the NaCl encryption library. The one or more servers may be used for and/or provide cloud and/or network computing. Although not shown in the figures, the one or more servers may have connections to external systems providing messaging functionality such as e-mail, SMS messaging, text messaging, and other functionalities, such as encryption/decryption services, cyber alerts, etc.

The one or more servers may be connected to or may be integrated with one or more databases. The one or more databases may include a cloud database or a database managed by a database management system (DBMS). In general, a cloud database may operate on platforms such as Python. A DBMS may be implemented as an engine that controls organization, storage, management, and retrieval of data in a database. DBMSs frequently provide the ability to query, backup and replicate, enforce rules, provide security, do computation, perform change and access logging, and automate optimization. A DBMS typically includes a modeling language, data structure, database query language, and transaction mechanism. The modeling language may be used to define the schema of each database in the DBMS, according to the database model, which may include a hierarchical model, network model, relational model, object model, or some other applicable known or convenient organization. Data structures can include fields, records, files, objects, and any other applicable known or convenient structures for storing data. A DBMS may also include metadata about the data that is stored.

Embodiments and all of the functional operations and/or actions described in this specification may be implemented in digital electronic circuitry, or in computer software, firmware, or hardware, including the structures disclosed in this specification and their structural equivalents, or in combinations of one or more of them. Embodiments may be implemented as one or more computer program products, for example, one or more modules of computer program instructions encoded on a computer readable medium for execution by, or to control the operation of, data processing apparatus. The computer-readable medium may be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, for example, code that constitutes processor firmware, a protocol stack, a database management system, an operating system, or a combination of one or more of them. A propagated signal is an artificially generated signal, for example, a machine-generated electrical, optical, or electromagnetic signal that is generated to encode information for transmission to a suitable receiver apparatus.

A computer program, also known as a program, software, software app, script, or code, may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data in a single file dedicated to the program in question, or in multiple coordinated files. A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform actions by operating on input data and generating output. The processes and logic flows may also be performed by, and apparatus may also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. A processor may include any suitable combination of hardware and software.

Elements of a computer may include a processor for performing instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. Moreover, a computer may be embedded in another device, for example, a user device. Computer-readable media suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto optical disks; and CD ROM and DVD-ROM disks. The processor and the memory may be supplemented by, or incorporated in, special purpose logic circuitry.

While this specification contains many specifics, these should not be construed as limitations on the scope of the disclosure or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and may even be claimed as such, one or more features from a claimed combination may in some cases be excised from the combination, and the claimed combination may be directed to a sub-combination or variation of a sub-combination.

Similarly, while actions are depicted in the drawings in a particular order, this should not be understood as requiring that such actions be performed in the particular order shown or in sequential order, or that all illustrated actions be performed, to achieve desirable results. Moreover, the separation of various system components in the embodiments described above should not be understood as requiring such separation in all embodiments, and it should be understood that the described program components and systems may generally be integrated together in a single software product or packaged into multiple software products.

It should be understood that the phrase one or more of and the phrase at least one of include any combination of elements. For example, the phrase one or more of A and B includes A, B, or both A and B. Similarly, the phrase at least one of A and B includes A, B, or both A and B.

Thus, particular implementations have been described. Other implementations are within the scope of the following claims. For example, the actions recited in the claims may be performed in a different order and still achieve desirable results.

What is claimed is:

1. A computer-implemented method comprising:
transmitting, by one or more processors, a request to register a user device and an application configured to be executed by the user device with one or more data sources, the request comprising timing permissions indicating when content is to be received for the application and data format information indicating a particular data format to be used for information provided to the application;
determining one or more trigger events associated with the registered application based on a type of the application;
receiving event information from the one or more data sources, and
determining that one of the one or more trigger events associated with the registered application has occurred based on the event information received from the one or more data sources;
in response to determining that one of the one or more trigger events has occurred, determining, by the one or more processors and using one or more neural networks, whether to output a notification including data corresponding to the event information based on one or more criteria, the one or more criteria including the timing permissions, the particular data format, and the user preferences;
in response to determining that the one or more criteria is satisfied, determining to output the notification including data corresponding to the event information; and
providing, by the one or more processors, the notification including the data corresponding to the event information to a display of a user device.

2. The computer-implemented method of claim 1, further comprising:
applying, by the one or more processors, the one or more neural networks and training data to train a notification generator to determine whether or not to output the notification, the training data including one or more of rules and permissions associated with the application, user preference data, user history data, and application trends.

3. The computer-implemented method of claim 1, further comprising:
receiving an indication that the application is not registered with the one or more data sources;
in response to receiving the indication that the application is not registered with the one or more data sources, determining, by the one or more processors, user preferences associated with the application;
determining, by the one or more processors, information that is likely to be of interest to the user based on the user preferences associated with the application; and
transmitting the request to register the application with the one or more data sources, wherein the request to register the application with the one or more data sources includes a request for data corresponding to the information that is likely to be of interest to the user.

4. The computer-implemented method of claim 1, further comprising:
determining, by the one or more processors, applications stored on the user device;
determining, by the one or more processors, application permissions and a trust level associated with each of the applications stored on the user device; and
in response to receiving an indication that the application is not registered with the one or more data sources:
determining, by the one or more processors, that receiving information from the one or more data sources satisfies the application permissions and the trust level for the application; and
transmitting the request to register the application with one or more data sources.

5. The computer-implemented method of claim 1, wherein the one or more trigger events associated with the application include:
a user action, expiration of a time period associated with the application, satisfaction of a condition set by rules of the application, and addition of data in the one or more data sources.

6. The computer-implemented method of claim 1, further comprising:
in response to providing the notification to the display of the user device, receiving an indication of a user selection at the user device; and
training, by the one or more processors, a notification generator to determine whether or not to output the notification using the user selection.

7. The computer-implemented method of claim 1, wherein providing, by the one or more processors, the notification including the data corresponding to the event information comprises:
selecting a template from a plurality of templates based on the type of the application; and
providing template data corresponding to the selected template to generate the notification.

8. One or more non-transitory computer-readable storage media comprising instructions, which, when executed by one or more computing devices, cause the one or more computing devices to perform operations comprising:
transmitting a request to register a user device and an application configured to be executed by the user device with one or more data sources, the request comprising timing permissions indicating when content is to be received for the application and data format information indicating a particular data format to be used for information provided to the application;
determining one or more trigger events associated with the registered application based on a type of the application;
receiving event information from the one or more data sources, and
determining that one of the one or more trigger events associated with registered application has occurred based on the event information received from the one or more data sources;
in response to determining that one of the one or more trigger events has occurred, determining, using one or more neural networks, whether to output a notification including data corresponding to the event information based on one or more criteria, the one or more criteria including the timing permissions, the particular data format, and the user preferences;
in response to determining that the one or more criteria is satisfied, determining to output the notification including data corresponding to the event information; and
providing the notification including the data corresponding to the event information to a display of a user device.

9. The one or more non-transitory computer-readable storage media of claim 8, wherein the operations further comprise:
applying the one or more neural networks and training data to train a notification generator to determine whether or not to output the notification, the training data including one or more of rules and permissions associated with the application, user preference data, user history data, and application trends.

10. The one or more non-transitory computer-readable storage media of claim 8, wherein the operations further comprise:
   receiving an indication that the application is not registered with the one or more data sources;
   in response to receiving the indication that the application is not registered with the one or more data sources, determining user preferences associated with the application;
   determining information that is likely to be of interest to the user based on the user preferences associated with the application; and
   transmitting the request to register the application with the one or more data sources, wherein the request to register the application with the one or more data sources includes a request for data corresponding to the information that is likely to be of interest to the user.

11. The one or more non-transitory computer-readable storage media of claim 8, wherein the operations further comprise:
   determining applications stored on the user device;
   determining application permissions and a trust level associated with each of the applications stored on the user device; and
   in response to receiving an indication that the application is not registered with the one or more data sources:
      determining that receiving information from the one or more data sources satisfies the application permissions and the trust level for the application; and
      transmitting the request to register the application with one or more data sources.

12. The one or more non-transitory computer-readable storage media of claim 8, wherein the one or more trigger events associated with the application include: a user action, expiration of a time period associated with the application, satisfaction of a condition set by rules of the application, and addition of data in the one or more data sources.

13. The one or more non-transitory computer-readable storage media of claim 8, wherein the operations further comprise:
   in response to providing the notification to the display of the user device, receiving an indication of a user selection at the user device; and
   training a notification generator to determine whether or not to output the notification using the user selection.

14. The one or more non-transitory computer-readable storage media of claim 8, wherein providing the notification including the data corresponding to the event information comprises:
   selecting a template from a plurality of templates based on the type of the application; and
   providing template data corresponding to the selected template to generate the notification.

15. A system comprising:
   one or more computing devices and one or more storage devices storing instructions which when executed by the one or more computing devices, cause the one or more computing devices to perform operations comprising:
      transmitting a request to register a user device and an application configured to be executed by the user device with one or more data sources, the request comprising timing permissions indicating when content is to be received for the application and data format information indicating a particular data format to be used for information provided to the application;
      determining one or more trigger events associated with the registered application based on a type of the application;
      receiving event information from the one or more data sources, and
      determining that one of the one or more trigger events associated with the registered application has occurred based on the event information received from the one or more data sources;
      in response to determining that one of the one or more trigger events has occurred, determining, and using one or more neural networks, whether to output a notification including data corresponding to the event information based on one or more criteria, the one or more criteria including the timing permissions, the particular data format, and the user preferences;
      in response to determining that the one or more criteria is satisfied, determining to output the notification including data corresponding to the event information; and
      providing the notification including the data corresponding to the event information to a display of a user device.

16. The system of claim 15, wherein the operations further comprise:
   applying the one or more neural networks and training data to train a notification generator to determine whether or not to output the notification, the training data including one or more of rules and permissions associated with the application, user preference data, user history data, and application trends.

17. The system of claim 15, wherein the operations further comprise:
   receiving an indication that the application is not registered with the one or more data sources;
   in response to receiving the indication that the application is not registered with the one or more data sources, determining user preferences associated with the application;
   determining information that is likely to be of interest to the user based on the user preferences associated with the application; and
   transmitting the request to register the application with the one or more data sources, wherein the request to register the application with the one or more data sources includes a request for data corresponding to the information that is likely to be of interest to the user.

18. The system of claim 15, wherein the operations further comprise:
   determining applications stored on the user device;
   determining application permissions and a trust level associated with each of the applications stored on the user device; and
   in response to receiving an indication that the application is not registered with the one or more data sources:
      determining that receiving information from the one or more data sources satisfies the application permissions and the trust level for the application; and
      transmitting the request to register the application with one or more data sources.

19. The system of claim 15, wherein the operations further comprise:

in response to providing the notification to the display of the user device, receiving an indication of a user selection at the user device; and training a notification generator to determine whether or not to output the notification using the user selection.

20. The system of claim 15, wherein providing the notification including the data corresponding to the event information comprises:

selecting a template from a plurality of templates based on the type of the application; and providing template data corresponding to the selected template to generate the notification.

* * * * *

UNITED STATES PATENT AND TRADEMARK OFFICE
CERTIFICATE OF CORRECTION

PATENT NO. : 10,397,163 B2
APPLICATION NO. : 15/345328
DATED : August 27, 2019
INVENTOR(S) : Carbune et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this
Second Day of June, 2020

Andrei Iancu
*Director of the United States Patent and Trademark Office*